United States Patent [19]

Mayes et al.

[11] Patent Number: 4,799,597

[45] Date of Patent: Jan. 24, 1989

[54] CONTAINER AND NON-REMOVABLE COVER

[75] Inventors: Ronald A. Mayes, San Anselmo, Calif.; Tipton A. Golias, Beaumont, Tex.

[73] Assignee: Helena Laboratories Corporation, Beaumont, Tex.

[21] Appl. No.: 128,616

[22] Filed: Dec. 4, 1987

Related U.S. Application Data

[62] Division of Ser. No. 12,900, Feb. 10, 1987, Pat. No. 4,736,859.

[51] Int. Cl.⁴ ............................................. B65D 41/04
[52] U.S. Cl. .................................. 215/250; 215/330; 215/356
[58] Field of Search ........................... 4/144.1, 144.2; 215/316, 330, 250, 356

[56] References Cited

U.S. PATENT DOCUMENTS

| | | | |
|---|---|---|---|
| 3,682,345 | 8/1972 | Baugh | 215/330 |
| 4,176,412 | 12/1979 | Peterson | 4/144.1 |
| 4,289,248 | 9/1981 | Lynn | 215/330 |

FOREIGN PATENT DOCUMENTS 847332 9/1960 United Kingdom ................ 215/250

Primary Examiner—Donald F. Norton
Attorney, Agent, or Firm—Phillips, Moore, Lempio & Finley

[57] ABSTRACT

A specimen collection apparatus particularly useful for urine samples. The apparatus includes a container or beaker and a screw on self-locking top that cannot be removed without damage to the top of the beaker.

8 Claims, 4 Drawing Sheets

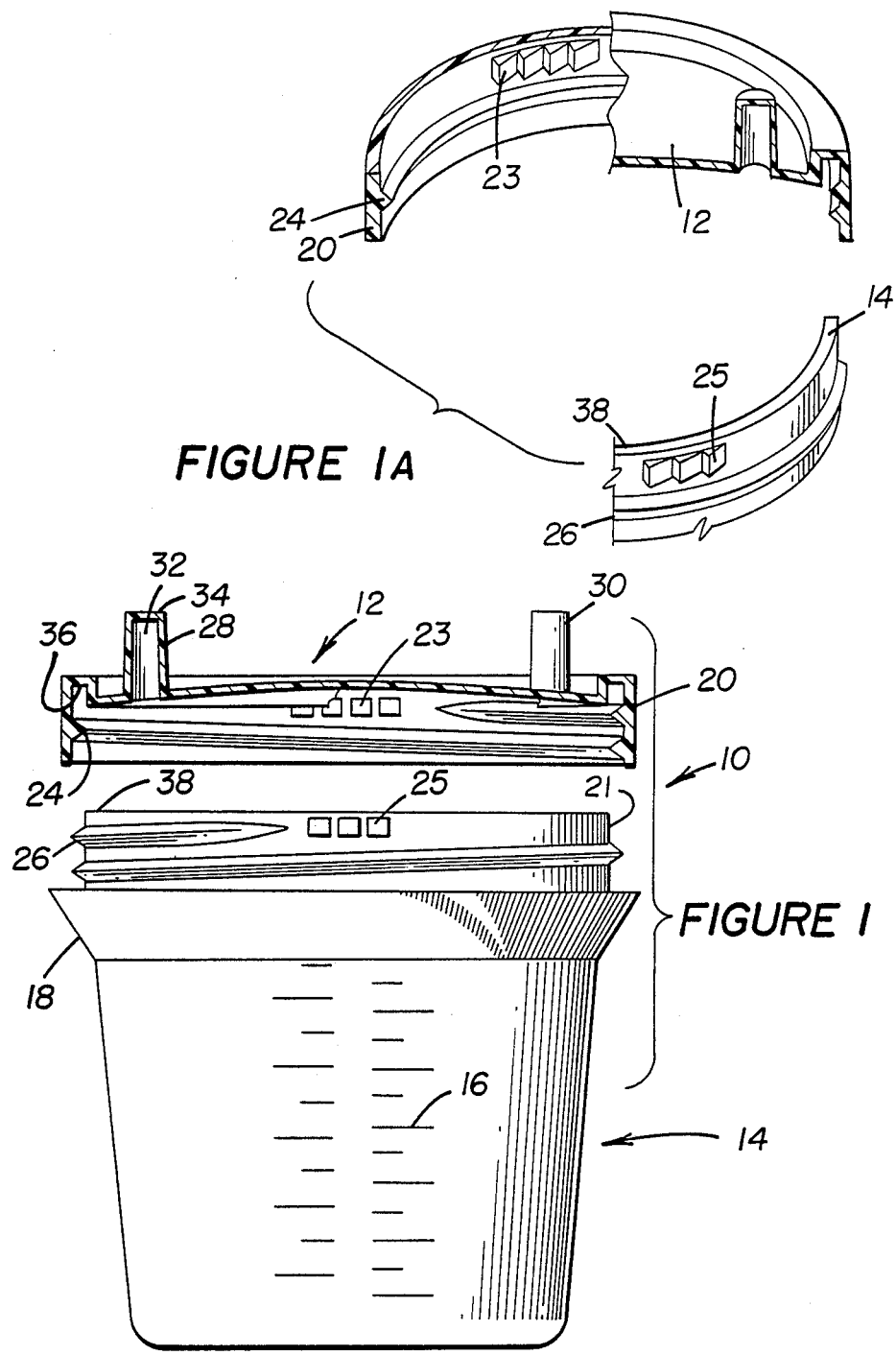

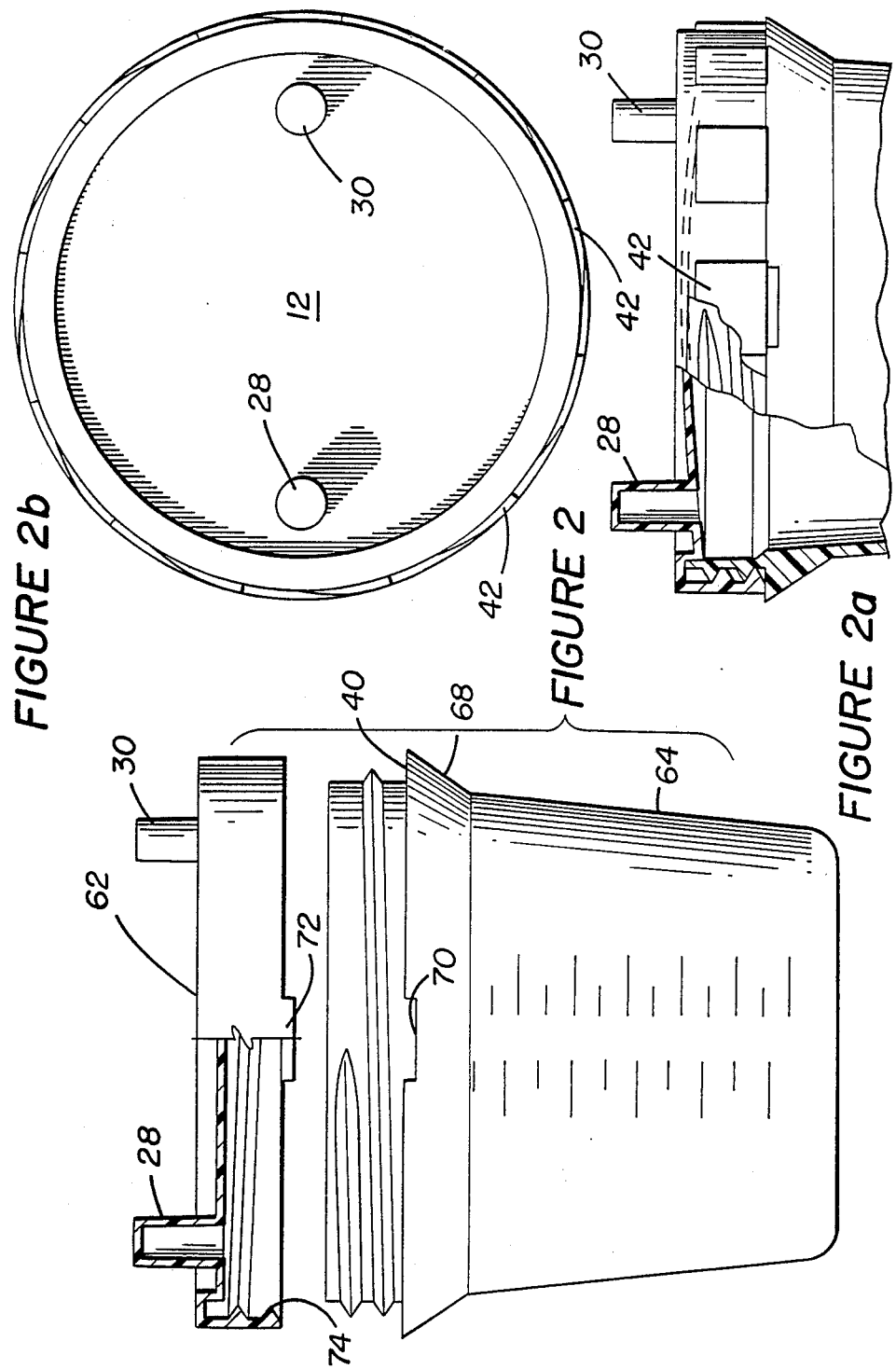

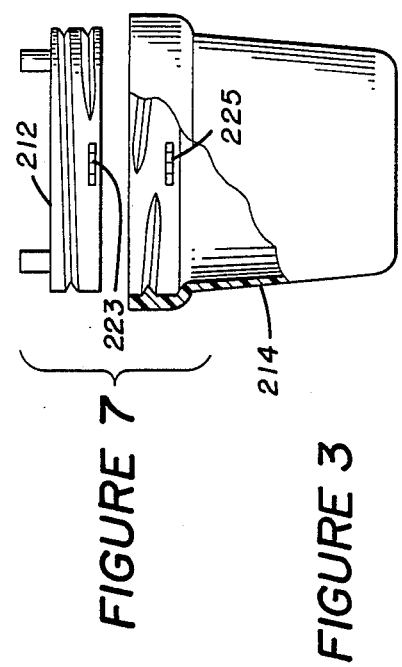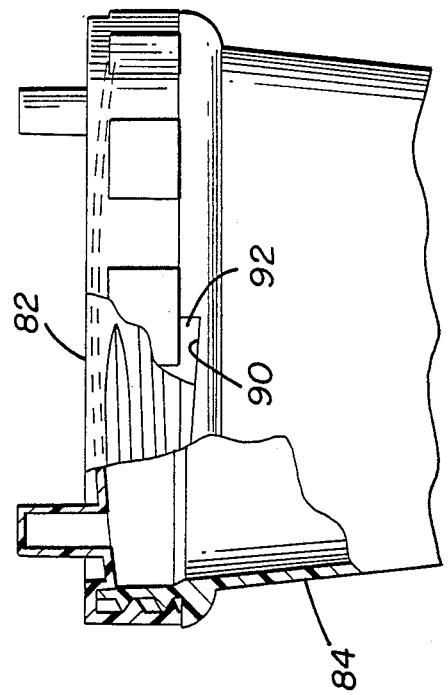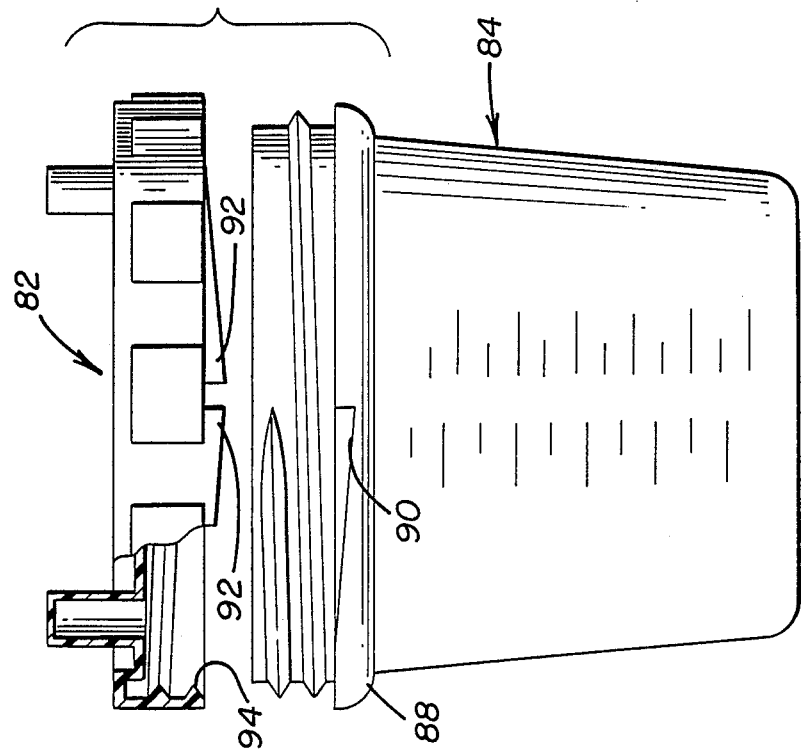

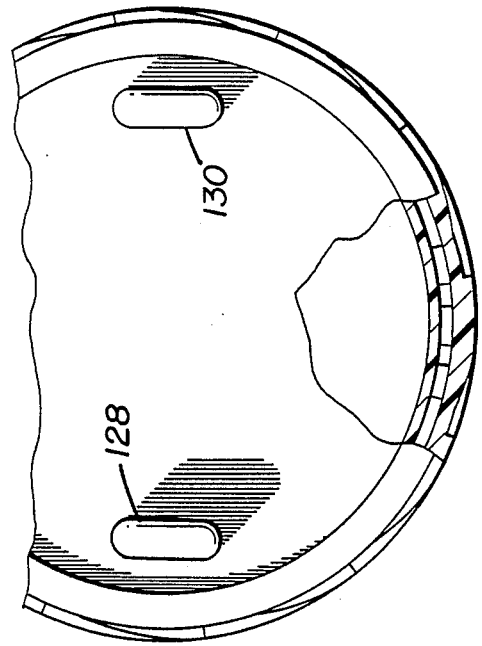
FIGURE 6
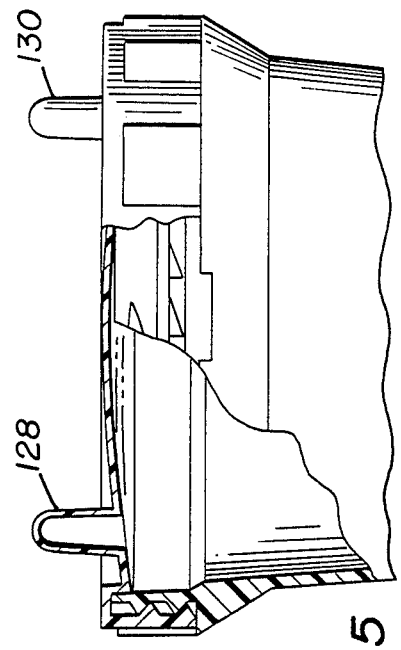
FIGURE 5
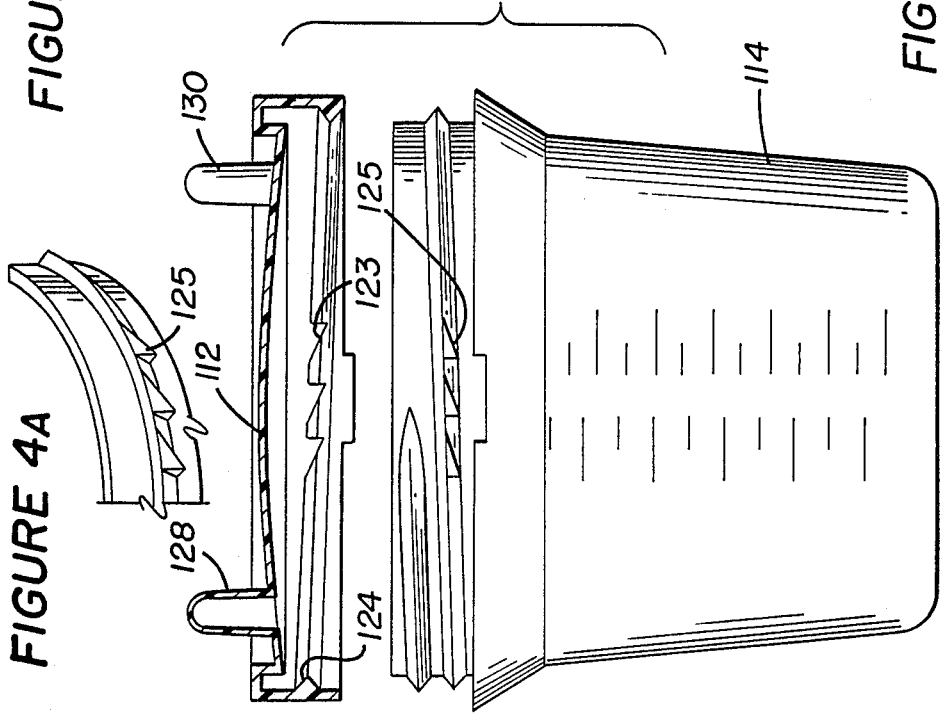
FIGURE 4
FIGURE 4A

CONTAINER AND NON-REMOVABLE COVER

This is a division of Ser. No. 012,900 filed Feb. 10, 1987 now U.S. Pat. No. 4,736,859.

DESCRIPTION

1. Technical Field

This invention relates to a container useful as a specimen collection apparatus and in particular relates to a specimen collection apparatus having a specially configured top which provides for both closure and sealing of the container so that the top may not be removed.

2. Background Art

The collection of specimens from individuals is a routine function in the diagnosis of human ailments and the like. Such specimens may consist of bodily waste products in various forms. Most prevalant is the collection of urine specimens. In the past such specimens have been collected in various types of containers including glass bottles and more recently disposable plastic containers. Such containers have always included a removable top which in some instances is replaceable. Recent tests have been developed to test for the presence of toxic substances such as drugs or alcoholism in the human body. Some of these tests include testing of a urine specimen. Since the ramification of such tests may have a lasting legal effect, it is important that the integrity of the sample be maintained.

While glass bottles have classically been used for urine sample collection, the very reason for using glass; i.e. reuse of the container, is contraindicated where the specimen must be protected.

Because of the expense and inconvenience associated with glass collection devices, laboratories have in some cases turned to paper and plastic disposable devices. Paper cup containers, generally without a cover, are used sometimes for some of the less elaborate tests by smaller facilities. Paper cups have most of the drawbacks of the glass containers. While they are not breakable and are inexpensive, they suffer from the same removable and reuseable or reclosable top and thus are inappropriate where security is important.

Plastic specimen collection apparatus generally consist of a beaker and some type of reclosable cover. For example, in one embodiment the cover is a snap-on variety which not only fails the security test but also poses particular problems to both the user and the technician in that the contents may be inadvertently spilled either when the top is "snapped on" the container or "snapped off" the container. An example of this embodiment is disclosed in U.S. Pat. No. 4,211,749 issued to Hans-Joachim Kantner on July 8, 1980.

Other urine sample containers and specimen collection apparatus generally encompass a beaker and a removeable top in the manner already described. The tops of the plastic collection containers may be of the snap-on type or a screw on variety. Further, provision is generally not made for a fluid-tight cover to prevent the collected sample from being spilled if the container is overturned. In some tests, spillage in the laboratory can result in contamination of the laboratory bench and possibly other samples.

Accordingly, it is appropriate to have a specimen collection apparatus that has a non-removable fluid-tight cover and, further one that is relatively inexpensive to manufacture and hence may be disposed of after a single use.

DISCLOSURE OF THE INVENTION

The present invention is directed toward overcoming one or more of the problems as set forth above. In one aspect of this invention a container is disclosed that includes a beaker having a body portion and a cover having a top portion. Interengaging means are provided both in the cover and on the beaker for connecting and fixedly sealing the cover to the beaker such that removal of the cover once it is fixed to the beaker is precluded.

BRIEF DESCRIPTION OF THE DRAWINGS

FIG. 1 is an elevation view partially in section of the preferred embodiment of the container or specimen collection apparatus disclosed here and showing the cover in relation to the body portion.

FIG. 1A is perspective view of portions of the same container shown in FIG. 1 showing the locking machanism.

FIG. 2 is an elevation view of an alternate embodimet of the container or specimen collection apparatus disclosed herein.

FIG. 2A is an elevation view of the specimen collection apparatus shown in FIG. 2 with the top in place on the container.

FIG. 2B is a top view of the cover of the container.

FIG. 3 is an elevation view of still another embodiment of the container or specimen collection apparatus disclosed herein.

FIG. 3a is an elevation view of the specimen collection apparatus of FIG. 3 with the top in place.

FIG. 4 is a third embodiment of the container or specimen collection apparatus.

FIG. 4a is a partial perspective view of a portion of the cover shown in FIG. 4.

FIG. 5 is still another embodiment of the container or specimen collection apparatus disclosed herein.

FIG. 6 is a top view of an alternate configuration of the top.

FIG. 7 is still another configuration wherein the top is formed as a plug.

BEST MODE OF CARRYING OUT THE INVENTION

Referring to FIG. 1, a container or specimen collection apparatus 10 is shown partially in section. Container or specimen collection apparatus 10 consists of a cover or top 12 and the bottom or beaker 14. Beaker 14 may be made of an appropriate plastic material by injection molding or the like and can include indices 16 to indicate the approximate contents of the beaker. Beaker 14 is, for example, adapted to receive approximately 100 millileters of a fluid sample such as urine or the like. Other capacities may also be provided. Formed near the top portion of beaker 14 is a shoulder 18, which acts to stiffen the beaker in all embodiments.

Top 12 and beaker 14 have integrally molded thereon mating threads 24 and 26 respectively so that top 12 being the female member may be threaded onto the threads 26 of the male member formed around the periphery of the top of beaker 14 above shoulder 18.

Formed in top 12 are a series of ramp like projections or ratchet teeth 23 inside and near the top of the downwardly projecting side wall 20 of top 12. Preferably there are four such teeth although at a minimum one tooth would suffice. Correspondingly, near the top of the outside of upstanding portion 21 of beaker 14 are a series of ramp like projections or ratchet teeth 25. Preferably there are three of these teeth although one tooth would suffice. The position of teeth 23 and teeth 24 are purposely located near the top of the beaker; and the inside of the top and beyond the end of the molded-in threads 24 and 26 so that when the top 12 is screwed on to beaker 14, the ratchet teeth 23 engage the ratchet teeth 25 just as top 2 is snugged down tight on beaker 14. With this structure, removal of the top is only possible by destruction of the cover.

Top 12 is formed with at least one and preferably two upstanding projections 28 and 30. Each projection such as projection 28 is formed with a hollow cavity 32 interior thereof. The top portion 34 of each projection may be thinner wall than the side walls of the projection in order to facilitate access into the hollow cavity 32 by means of a probe or suction device.

Top 12 is formed such that a channel 36 is formed around the interior of the inner edge of top 12 above the threads 24. The channel 36 receives the upper periphery of 38 of beaker 14 so that the inner side of the periphery 38 abuts closely the inner portion of channel 36 thereby forming a relatively fluid tight seal when the threads 24 of the top 12 are snugged down on the threads 26 of beaker 14.

During subsequent laboratory testing the top 34 of projection 28, or 30 as appropriate, may be removed with a knife or the like or punctured by a needle at the end of a syringe in order to withdraw samples from the container. Of course if the top is tampered with, which would be evidenced by tearing or breaking of the top, then the laboratory technician can presume that the sample has been adulterated and take appropriate action.

Top 12 is formed with a series of ramp-like projections of 42 around the outer periphery thereof (see e.g. FIGS. 1b and 2a) in order to facilitate fixing the top 12 on beaker 14. As noted, the caming action of the teeth 23 and 25 as the top is placed on the beaker will create a certain degree of resistance and it is appropriate to provide a means for grasping the top and rotating it against this resistance. The ramp-like projections 42 serve this function. It is pointed out that the ramp-like projections are formed so that the advantage to the user is rotation in only one direction.

DESCRIPTION OF THE SECOND EMBODIMENT

In a second embodiment a boss 72 is formed on top 62 (see FIG. 2) along with an indentation 70 on shoulder 68 of the beaker 64. In particular the boss 72 will ride around the upper surface 40 of shoulder 68 until it comes into register with the indentation 70. The corresponding boss 72 and indentation 70 on diametrically opposite sides of top 62 and beaker 65 result in a caming motion as the top is rotated onto the beaker. It should be pointed out that the flexibility of the plastic material is such that disengagement of the threads 24 and 26 does not occur before the bosses 72 seat in indentations 70. This condition is shown in FIG. 2A. Once the bosses 72 are seated in indentations 70 then, again, the resiliency of the plastic material forming the beaker and top is such that it is not possible to rotate the top in a counter clockwise direction in order to remove the top from the beaker without damage. In short the top 62 has become permanently affixed to beaker 64 so that the sample collected in beaker 64 cannot be tampered with except by destruction of the container.

DESCRIPTION OF THE THIRD EMBODIMENT

Referring now to FIG. 2 the same beaker 84 is illustrated along with the top 82. The structure of the beaker and the top are essentially the same, however, the shoulder 88 is formed with a ramp-like indentation 90 which corresponds to a ramp-like downwardly directed projection 92 on the top 82. As can be seen rotation of top 82 about the beaker 84 with the threads 94 engaged with the corresponding threads 96 causes the ramp 92 to cam around the shoulder 88 coming into engagement with the indentation 90. Once engaged with the indentation 90, the top portion 82 is essentially prevented from rotation in the same manner as the primary embodiment shown in FIG. 1.

FOURTH EMBODIMENT

Still a fourth embodiment is shown in FIG. 4 wherein the beaker 114 contains a plurality of downwardly extending ratchet-like teeth 125 as shown in FIG. 4. Corresponding openings are formed in the female thread 124 of top 112 as shown in FIG. 4. These openings or indentations 123 receive the teeth or projections 125 just as the top 112 is snugged down on to beaker 114. As can be seen in FIG. 4, once this occurs the top 112 cannot be removed from beaker 114.

Combinations of the Embodiments

As shown in FIG. 5, the embodiment illustrated in FIG. 2 with the boss 72 and indentation 70 on the top 62 and beaker 64 respectively may be used in combination with one of the other embodiments or conversely any two or more of the other embodiments may be used together in combination. The principal function of all the embodiments is to prevent removal of the top 62 once it is seated upon the beaker 64. While it has been found that the various means for retaining the top 62 on beaker 64 work independently, a combination of two or more of the embodiments may be appropriate in certain instances.

A slightly different arrangement for the upwardly extending projections 128 and 130 is shown if FIGS. 4, 5 and 6. In the embodiments shown in FIGS. 4, 5 and 6, the projections have a generally rectangular shape such that a test paper may be inserted through the snipped off top of either or both of the projections.

Finally, as shown in the embodiments discussed to this point, the top portion 12 may be bowed slightly when in engagement with the beaker 14 so that the channel 36 forces the outer periphery 38 of the beaker 14 outwardly when the top is in engagement with the beaker. This assists in forming a tight seal between the top and the beaker.

This invention has been described in relation to a container or beaker having an external thread at the top to receive a cover that is internally threaded. In conjunction with the beaker and the cover, means are provided to lock the cover to the beaker once it is screwed on. Also included within the concept of this invention (see FIG. 7) is a beaker 214 having internal threads at the top and a plug like top 212 having external threads, the two incorporating one or more of the means described herein such as ratchet teeth 223 and 225 to lockingly retain the plug in the top of the beaker.

While this invention has been described in relation to a primary and several alternate embodiments, it should be understood that it is to be limited only by the scope and content of the appended claims.

What we claim is:

1. A container comprising:
   a beaker having a body portion and including an upper periphery;
   a cover having a top portion, said cover including a downwardly extending skirt;
   first inter-engaging means unitarily formed in said cover and second inter-engaging means unitarily formed in said beaker, said first inter-engaging means comprising a formed thread on the exterior of said skirt, said second inter-engaging means comprising a formed thread about the inside of said upper periphery of said beaker, said first inter-engaging means further comprising at least one first rachet tooth formed on said skirt and said secnd inter-engaging means comprising at least one second rachet tooth formed on said beaker, said first and second inter-engaging means locking one with the other when said cover is positioned on said beaker whereby said cover becomes non-removable without damage to said beaker or said cover.

2. A container comprising:
   a beaker having a body portion, said body portion including an upper periphery;
   a cover having a top portion, said top portion including a downwardly extending skirt;
   first inter-engaging means unitarily formed in said cover and second inter-engaging means unitarily formed on said beaker;
   said second inter-engaging means formed on said beaker including a shoulder extending about said periphery, said shoulder including at least one indentation and further wherein said second inter-engaging means formed in said beaker includes formed threads about said periphery and above said shoulder;
   said first inter-engaging means formed in said cover including at least one boss extending downwardly from said skirt, said first inter-engaging means formed in said cover further including formed threads interior of said skirt and adapted to mate with the formed threads about the upper periphery of said beaker, said boss engagable with the at least one indentation so that said cover becomes non-removable without damage to said beaker and said cover when said cover is connected with said beaker.

3. The container of claim 2 wherein said top, when engaged with said beaker forms a relatively fluid tight joint between said top and said beaker.

4. A container comprising:
   a beaker having a body portion, said beaker also including an upper periphery with formed threads extending about said upper periphery, said formed threads including at least one rachet tooth formed in the threads;
   a cover having a top portion, said top portion including a downwardly extending skirt and further including formed threads about said skirt and at least one rachet tooth formed in said formed threads, said rachet tooth formed in said top portion adapted to lock into the at least one rachet tooth formed in the threads about the upper periphery of said beaker so that said cover becomes non-removable when connected with said beaker without damage to said beaker or said cover.

5. The container of claim 4 wherein the formed threads of said beaker are on the outer circumference of said beaker and further wherein the formed threads of said top are on the inner circumference of said downwardly extending skirt.

6. The container of claim 5 further defining a shoulder extending about said upper periphery of said beaker below said formed threads.

7. The container of claim 4 wherein the formed threads on said beaker are in the inner circumference of the upper periphery of said beaker and wherein the formed threads of said top are on the outer perimeter of said downwardly extending skirt.

8. A container comprising:
   a beaker having a body portion and an upper periphery;
   a cover having a top portion, having a downwardly extending skirt;
   first inter-engaging means unitarily formed in said cover and second inter-engaging means unitarily formed in said beaker, said second inter-engaging means including a shoulder extending about said upper periphery, said shoulder including at least one ramp-like indentation, said periphery having a formed thread thereabout;
   said cover having a formed thread about its interior and engagable with said formed thread about said beaker periphery, said skirt further including a downwardly extending ramp-like projection formed to lockingly mate with said ramp-like indentation in said shoulder with said top threadably engaged with said beaker.

* * * * *